United States Patent [19]

Cella

[11] 4,386,222
[45] May 31, 1983

[54] METHOD FOR MAKING KETO ACIDS AND DIONE CYCLICS OBTAINED THEREFROM

[75] Inventor: James A. Cella, Clifton Park, N.Y.

[73] Assignee: General Electric Company, Schenectady, N.Y.

[21] Appl. No.: 327,339

[22] Filed: Dec. 4, 1981

Related U.S. Application Data

[62] Division of Ser. No. 182,999, Sep. 2, 1980, Pat. No. 4,340,753.

[51] Int. Cl.$^3$ ............................................. C07C 45/66
[52] U.S. Cl. ..................................... 568/346; 562/527
[58] Field of Search ................. 562/527, 528; 568/346

[56] References Cited

U.S. PATENT DOCUMENTS

| | | | |
|---|---|---|---|
| 2,938,918 | 5/1980 | Lavigne | 562/528 |
| 3,419,605 | 12/1968 | Mead | 562/528 |
| 3,468,944 | 9/1969 | Chafety et al. | 562/528 |
| 3,590,080 | 6/1971 | Beesley et al. | 562/528 |

OTHER PUBLICATIONS

Blaha et al., Coll. Czech. Chem. Comm., vol. 30, pp. 1214–1219 (1965).
Henshall et al., J.A.C.S., vol. 77, pp. 6656–6658 (1955).

*Primary Examiner*—James H. Reamer
*Attorney, Agent, or Firm*—William A. Teoli; James C. Davis, Jr.; James Magee, Jr.

[57] ABSTRACT

A method is provided for oxidatively cleaving $\alpha,\beta$-unsaturated cyclic ketones, such as isophorone, with an oxidizing agent, for example, ozone, and thereafter recovering the resulting keto acid. In instances where ozone is used, an aqueous hydroperoxide and phase transfer catalyst can be used to recover the keto acid. Dione cyclics, for example, dimedone, can be obtained by direct dehydration of the keto acid.

1 Claim, No Drawings

METHOD FOR MAKING KETO ACIDS AND DIONE CYCLICS OBTAINED THEREFROM

This application is a division of application Ser. No. 182,999, filed Sept. 2, 1980, now U.S. Pat. No. 4,340,753.

BACKGROUND OF THE INVENTION

The present invention relates to a method for making keto acids by oxidatively cleaving an α,β-unsaturated ketones such as isophorone which thereafter can be converted to dimedone by the dehydration of the resulting keto acid.

Prior to the present invention, dimedone, or 5,5-dimethylcyclohexane-1,3-dione, as shown by the following formula,

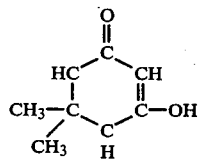

was used to make various silyl ethers, in accordance with my invention, as shown by U.S. Pat. No. 4,210,596. These silylethers are useful as RTV curing agents for making moisture curable organopolysiloxanes, as shown by U.S. Pat. Nos. 4,176,111 and 4,176,112, assigned to the same assignee as the present invention. One method for making dimedone is based on the cyclization of the corresponding keto acid or ester, as shown by Blaha et al, Czech. Pat. No. 116,788 and Blaha et al, Collection Czech. Chem. Comm., 30, 1214 (1965). The aforementioned procedure of Blaha, however, is economically unattractive due to the high material costs, since the keto acids which are cyclized generally have been obtained by a condensation reaction of an acetic acid equivalent and mesityl oxide, or an acrylate with an acetone equivalent. Considerable effort has therefore been expended to determine satisfactory methods for making 5-keto-3,3-dimethylhexanoic acid which is the precursor of dimedone.

The present invention is based on the discovery that isophorone, an α,β-unsaturated ketone having the formula,

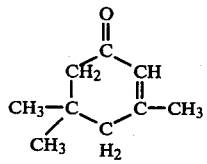

can be oxidatively cleaved with loss of the alpha carbon atom to produce 5-keto-3,3-dimethylhexanoic acid. In view of the fact that isophorone is a readily available commercial material derived from the condensation of acetone, a satisfactory technique for synthesizing dimedone is therefore available.

I have further discovered that a particularly attractive procedure for oxidatively cleaving isophorone and other α,β-unsaturated ketones is by the use of ozone. I have further found that cleavage of the resulting ozonide formed during the ozonolysis of the isophorone can be satisfactorily achieved by the use of hydrogen peroxide and an alkali metal hydroxide and a phase transfer catalyst, whereby the resulting keto acid is selectively extracted from the organic phase to the aqueous phase as it forms. As a result, there is no build-up of a potentially dangerous ozonide since it is readily decomposed as it is formed. The resulting keto acid can then be isolated satisfactorily by acidification of the aqueous phase.

STATEMENT OF THE INVENTION

In a method for making keto acid from α,β-unsaturated ketones by oxidative cleavage which prior to the present invention was accomplished by ozonolysis, whereby a hazardous α,β-unsaturated ketone ozonide intermediate was built-up in the reaction mixture, the improvement which comprises, (1) effecting the ozonolysis of the α,β-unsaturated ketone in an aqueous-organic solvent two phase mixture in the presence of an alkali metal hydroperoxide and a phase transfer catalyst, whereby the resulting keto acid is extacted to the aqueous phase as it is formed from decomposition of its ozonide produced in the organic phase, (2) acidifying the aqueous phase containing the keto acid alkali metal salt resulting in the precipitation of the keto acid and (3) recovering the resulting keto acid from the mixture of (2).

There is further provided by the present invention a method for making dimedone which comprises (4) oxidatively cleaving isophorone to produce 5-keto-3,3-dimethylhexanoic acid, and (5) dehydrating the keto acid of (4) utilizing sulfuric acid at a concentration of from 70 to 80% and at a temperature of from 100° C. to 150° C.

There are included by the α,β-unsaturated ketones which can be oxidatively cleaved by ozonolysis in accordance with the practice of the present invention compounds such as

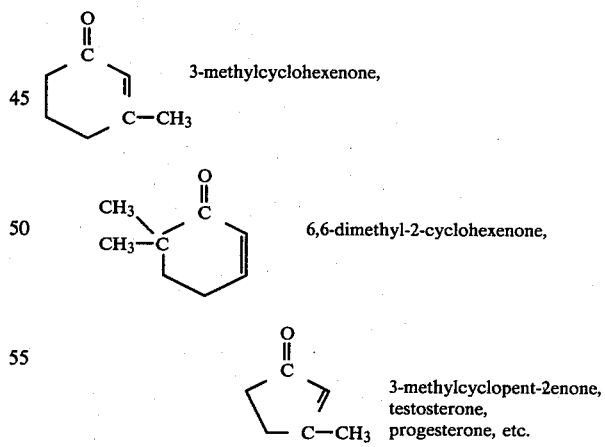

In addition to ozonolysis as previously described, the additional methods which can be used to oxidatively cleave isophorone are, for example, a mixture of ruthenium dioxide and an alkali metal hypochlorite.

The generation of the aqueous hydroperoxide anion employed in the above described ozonolysis method for effecting the decomposition of the ozonide results from a mixture of hydrogen peroxide having a concentration of from 3% to 50% and water and an alkali metal hydroxide, for example, sodium hydroxide, potassium hydroxide, etc. which can be utilized in equal molar amounts in the aqueous phase of the ozonolysis reaction mixture.

Some of the phase transfer catalysts which can be utilized in the oxidative cleavage method utilizing ozone as described above, are, for example, quaternary ammonium and phosphonium salts, such as described in JACS 93, 195 (1971) by C. M. Starks. A proportion of from about 0.001 to 0.1 moles of the phase transfer catalyst, per mole of the α,β-unsaturated ketone has been found to provide effective results and preferably from 0.01 to 0.05 moles of phase transfer catalyst per mole of α,β-unsaturated ketone can be employed.

In the practice of the invention, oxidative cleavage of the isophorone can be achieved by the use of a variety of olefin cleavage reagents including ruthenium tetroxide in combination with sodium periodate, sodium hypochlorite, a combination of potassium permanganate and sodium periodate, ozone, for the ozonolysis procedure, etc. Temperatures in the range of −20° C. to 35° C. can be used in the presence of a variety of organic solvents, for example, chloroform, methylene chloride, etc.

Preferably, the oxidative cleavage can be effected by ozonolysis which can be used in combination with a phase transfer catalyst and an alkali metal hydroperoxide. The following reaction scheme will serve to further illustrate the preferred procedure, where M is an alkali metal ion and R is a $C_{(1-16)}$ monovalent aliphatic organic radical or a $C_{(6-13)}$ aromatic organic radical:

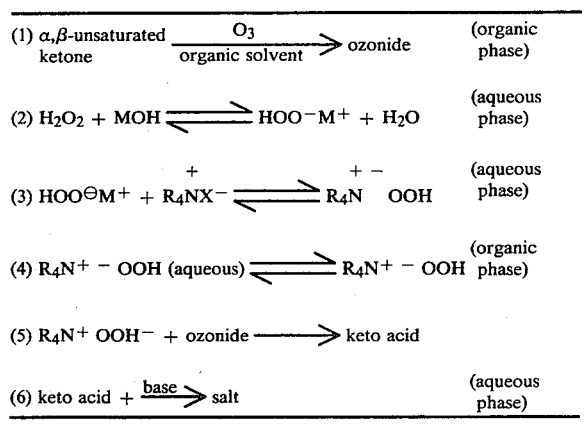

The cyclodehydration of the keto acid at (6) results in the formation of the 1,3-cyclodione. Preferably, sulfuric acid having a concentration of 70% to 80% is used at a temperature of 100° C. to 150° C. as taught by Henshall et al, J. Am. Chem. Soc. 77 6656 (1955).

In order that those skilled in the art will be better able to practice the invention, the following examples are given by way of illustration and not by way of limitation. All parts are by weight.

EXAMPLE 1

There was added 0.15 part of solid ruthenium oxide to a solution of 2.8 parts of isophorone and 2.5 parts of sodium periodate in about 200 parts of acetone to 40 parts of water. The resulting yellow solution was stirred while 5 parts of sodium periodate, 50 parts of water and 20 parts of acetone was added over an hour. The resulting suspension was stirred 48 hours at room temperature then filtered through Celite. The resulting filtrate was then extracted with methylene chloride. The organic phase was extracted with $CHCl_3$. Acidification of the base washings provided 2 parts, or a 63%, yield of 5-keto-3,3-dimethylhexanoic acid.

The above oxidation procedure was repeated, except that in place of periodate there was utilized sodium hypochlorite. There was added slowly about 2700 parts of an aqueous 5% sodium hypochlorite solution to a solution of 56 parts of isophorone in about 200 parts of methylene chloride. An exothermic reaction resulted causing the methylene chloride to reflux. The organic phase was analyzed shortly after the addition was complete and it was found that all of the isophorone had reacted. The aqueous layer was made basic with sodium carbonate and the reaction mixture was filtered. The aqueous phase was washed with methylene chloride and then acidified by slowly adding it to a 2 phase mixture of concentrated hydrochloric acid and methylene chloride. The organic phase was separated and the aqueous phase was extracted with several portions of fresh methylene chloride. Upon combining the various organic layers which were dried and evaporated, there was obtained 37.7 parts of 5-keto-3,3-dimethylhexanoic acid.

An additional procedure was used to oxidatively cleave the isophorone with ozone. Ozone was introduced into a mixture of 4.2 parts of isophorone and about 75 parts of methanol at a temperature of −60° C. Based on the analysis of the reaction mixture, complete reaction occurred approximately 1 hour after the addition of the ozone was complete. There was then added to the mixture about 10 parts of 0.6 N nitric acid solution and the resulting mixture was heated at 50°-60° C. for approximately 3 hours. At the completion of the reaction period a small portion of the mixture gave a negative starch iodide test. The mixture was extracted with ether and then the resulting keto acid was recovered as described above. There was obtained an 89.6% yield of the keto acid. Its identity was confirmed by NMR, IR and mass spectroscopy.

A solution of 5 parts of 5-keto-3,3-dimethylhexanoic acid and about 15 parts of 73% sulfuric acid was heated for one hour in a 130°-135° oil bath. The cooled solution was then poured into a separatory funnel containing ice and chloroform. The aqueous phase was then washed three times with additional chloroform. The combined organic extractions were then dried and evaporated. There was obtained an 82.3% yield of dimedone. It was further recrystallized from toluene.

EXAMPLE 2

Ozone generated in a Welsbach Ozonizer was introduced into a stirred mixture chilled to −5° C. consisting of 15 parts of isophorone, 15.5 parts of 30% hydrogen peroxide, 5.1 part of sodium hydroxide, 0.2 part of Adogen 464 (MW about 401) and about 25 parts of methylene chloride. The ozone was introduced until no more isophorone could be detected by gas chromatography. The mixture was then stirred an additional 2 hours and the aqueous phase was separated and acidified. There was obtained 12 parts or a 76% yield of 5-keto-3,3-dimethylhexanoic acid. In accordance with the procedure of Example 1, the aforementioned keto acid was dehydrated using sulfuric acid. There was obtained an 85% yield of dimedone.

EXAMPLE 3

Ozone was passed through a solution of 2.0 gms of 3-methyl-2-cyclohexenone at −78° C. for 30 minutes. The mixture was warmed to −20° C. and treated with a solution of 3.0 g of 30% hydrogen peroxide in 3.0 g of 50% NaOH. A drop of Adogen 464 was added and the two phase mixture was stirred vigorously for 1 hour. The aqueous phase was separated and acidified then extracted with ether. Removal of the ether afforded 1.12 g (48%) of 5-keto-hexanoic acid. The identity of the acid was confirmed by comparing the IR spectra of its methyl ester to the known spectra of the same compound.

The same procedure was repeated, except there was used 0.944 part of progesterone in place of the 3-methyl-2-cyclohexenone. There was obtained 0.84 part, or an 84% yield of product having a M.P. of 169°–171° C. Based on method of preparation and spectral data the product was

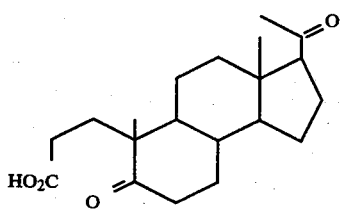

Similarly, 1.15 g of cholestenone afforded 0.9 g yield of the keto-acid having a m.p. of 147°–148° C. and the formula,

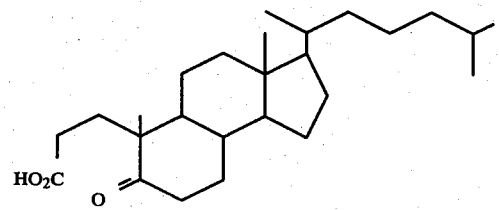

Although the above examples are directed to only a few of the very many variables utilized in the practice of the method of the present invention, it should be understood that the method of the present invention is directed to a much broader variety of α,β-unsaturated ketones to provide the corresponding keto acid in accordance with the ozonolysis of the present invention as well as other means of oxidatively cleaving isophorone to provide for reproduction of 5-keto-3,3-dimethylhexanoic acid and the cyclization of such keto acid to the corresponding 1,3-cyclic dione.

What I claim as new and desire to secure by Letters Patent of the United States is:

1. A method for making dimedone which comprises
   (1) oxidatively cleaving isophorone by ozonolysis in an aqueous organic solvent two-phase mixture in the presence of an alkali metal hydroperoxide in a phase transfer catalyst to produce 5-keto-3,3-dimethylhexanoic acid, and
   (2) dehydrating the keto acid of (1) utilizing sulfuric acid at a concentration of from 70 to 80% and at a temperature of from 100° C. to 150° C.

* * * * *